(12) United States Patent
Juhnke et al.

(10) Patent No.: US 10,564,129 B2
(45) Date of Patent: Feb. 18, 2020

(54) METHOD AND ARRANGEMENT FOR ACOUSTICALLY TESTING THE MECHANICAL INTEGRITY OF A CARTRIDGE

(71) Applicant: SANOFI-AVENTIS DEUTSCHLAND GMBH, Frankfurt am Main (DE)

(72) Inventors: Hanno Juhnke, Frankfurt am Main (DE); Jan-Peter Spengler, Frankfurt am Main (DE); Jasmin Groeschke, Frankfurt am Main (DE); Anne Boker, Frankfurt am Main (DE); Michael Fischer, Frankfurt am Main (DE); Matthias Scharf, Frankfurt am Main (DE); Michael Schrack, Pliezhausen (DE); Olaf Zeckai, Weinheim (DE); Jurgen Hemberger, Aschaffenburg (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 79 days.

(21) Appl. No.: 15/329,948

(22) PCT Filed: Aug. 4, 2015

(86) PCT No.: PCT/EP2015/067903
§ 371 (c)(1),
(2) Date: Jan. 27, 2017

(87) PCT Pub. No.: WO2016/020358
PCT Pub. Date: Feb. 11, 2016

(65) Prior Publication Data
US 2018/0017531 A1  Jan. 18, 2018

(30) Foreign Application Priority Data
Aug. 8, 2014 (EP) .................. 14180349

(51) Int. Cl.
*G01N 29/12* (2006.01)
*G01N 29/34* (2006.01)
(Continued)

(52) U.S. Cl.
CPC .......... *G01N 29/12* (2013.01); *A61M 5/2466* (2013.01); *G01N 29/28* (2013.01); *G01N 29/348* (2013.01);
(Continued)

(58) Field of Classification Search
CPC ........ A61M 5/20; G01H 17/00; G01M 7/025; G01N 29/12
See application file for complete search history.

(56) References Cited

U.S. PATENT DOCUMENTS 3,307,696 A * 3/1967 Sager ............... G01N 21/88
209/564
4,096,738 A 6/1978 Rupp et al.
(Continued)

FOREIGN PATENT DOCUMENTS

EP  0 278 074   8/1988
JP  S52-117685  10/1977
(Continued)

OTHER PUBLICATIONS

International Preliminary Report in International Application No. PCT/EP2015/067903, dated Feb. 14, 2017, 10 pages.
(Continued)

*Primary Examiner* — David A Rogers
(74) *Attorney, Agent, or Firm* — Fish & Richardson P.C.

(57) ABSTRACT

The present invention relates to a method of testing the mechanical integrity of a cartridge (10) containing a medicament and being arranged inside a drug delivery device (20). The invention also relates to a testing arrangement and to a respective drug delivery device, wherein the method
(Continued)

comprises the steps of: acoustically stimulating the cartridge (10), measuring of the cartridge's (10) acoustic response (60) to the acoustic stimulation (32), comparing the acoustic response (60) with a standard response (62) of an intact cartridge (10), and determining the mechanical integrity of the cartridge (10) on the basis of the comparison.

10 Claims, 5 Drawing Sheets

(51) Int. Cl.
*G01N 29/44* (2006.01)
*G01N 29/46* (2006.01)
*A61M 5/24* (2006.01)
*G01N 29/28* (2006.01)

(52) U.S. Cl.
CPC ......... *G01N 29/4427* (2013.01); *G01N 29/46* (2013.01); *A61M 2205/3375* (2013.01); *A61M 2205/50* (2013.01); *G01N 2291/0258* (2013.01); *G01N 2291/0289* (2013.01)

(56) References Cited

U.S. PATENT DOCUMENTS

| | | | | |
|---|---|---|---|---|
| 5,615,007 | A * | 3/1997 | Matsuura | G01N 21/90 356/237.1 |
| 6,319,225 | B1 * | 11/2001 | Sugita | A61M 5/2448 604/191 |
| 6,367,328 | B1 | 4/2002 | Gorman et al. | |
| 6,793,646 | B1 * | 9/2004 | Giambattista | A61M 5/2066 604/208 |
| 6,913,591 | B2 * | 7/2005 | Itoh | A61M 5/14566 604/67 |
| 7,291,132 | B2 * | 11/2007 | Deruntz | A61M 5/31551 604/207 |
| 7,674,246 | B2 * | 3/2010 | Gillespie | A61M 5/001 604/181 |
| 7,779,831 | B1 | 8/2010 | Von Hollen et al. | |
| 8,556,862 | B2 * | 10/2013 | Cronenberg | A61M 5/2066 604/195 |
| 8,961,455 | B2 * | 2/2015 | Holmqvist | A61M 5/2033 604/82 |
| 9,011,375 | B2 * | 4/2015 | Holmqvist | A61M 5/24 604/135 |
| 9,061,107 | B2 * | 6/2015 | Cronenberg | A61M 5/3294 |
| 9,753,015 | B2 * | 9/2017 | Bardina | G01M 7/022 |
| 9,833,578 | B2 * | 12/2017 | Elmen | A61M 5/2033 |
| 9,889,258 | B2 * | 2/2018 | Bengtsson | A61M 5/2033 |
| 9,962,490 | B2 * | 5/2018 | Karlsson | A61M 5/2033 |
| 2005/0049550 | A1 * | 3/2005 | Kirchhofer | A61M 5/2448 604/82 |
| 2005/0087016 | A1 * | 4/2005 | Gilmore | G01N 29/0609 73/579 |
| 2005/0209569 | A1 * | 9/2005 | Ishikawa | A61M 5/20 604/207 |
| 2011/0178500 | A1 * | 7/2011 | Shang | A61M 5/2033 604/506 |
| 2012/0233834 | A1 * | 9/2012 | Szechinski | B23P 19/04 29/407.01 |
| 2012/0289905 | A1 * | 11/2012 | Julian | A61M 5/20 604/189 |
| 2013/0072897 | A1 * | 3/2013 | Day | A61M 5/24 604/500 |
| 2013/0211326 | A1 * | 8/2013 | Dasbach | A61M 5/24 604/111 |
| 2013/0221097 | A1 * | 8/2013 | Day | A61M 5/20 235/437 |
| 2013/0226139 | A1 * | 8/2013 | Day | A61M 5/5086 604/506 |
| 2013/0289488 | A1 * | 10/2013 | Riess | A61M 5/24 604/189 |
| 2015/0253289 | A1 * | 9/2015 | Bardina | G01M 7/022 73/579 |

FOREIGN PATENT DOCUMENTS

| | | | | |
|---|---|---|---|---|
| JP | S61-073063 | | 4/1986 | |
| JP | H2-67956 | | 3/1990 | |
| JP | H05-045340 | | 2/1993 | |
| JP | H10-293123 | | 11/1998 | |
| JP | 2003284778 | A * | 10/2003 | |
| JP | 2009-92601 | | 4/2009 | |
| JP | 2014-137286 | | 7/2014 | |
| WO | WO 91/05250 | | 4/1991 | |
| WO | WO 2006/101944 | | 9/2006 | |
| WO | WO-2012089620 | A2 * | 7/2012 | ............. A61M 5/24 |
| WO | WO 2013/120778 | | 8/2013 | |
| WO | WO 2014/046148 | | 3/2014 | |
| WO | WO 2014/059240 | | 4/2014 | |

OTHER PUBLICATIONS

International Search Report and Written Opinion in International Application No. PCT/EP2015/067903, dated Mar. 31, 2016, 15 pages.

* cited by examiner

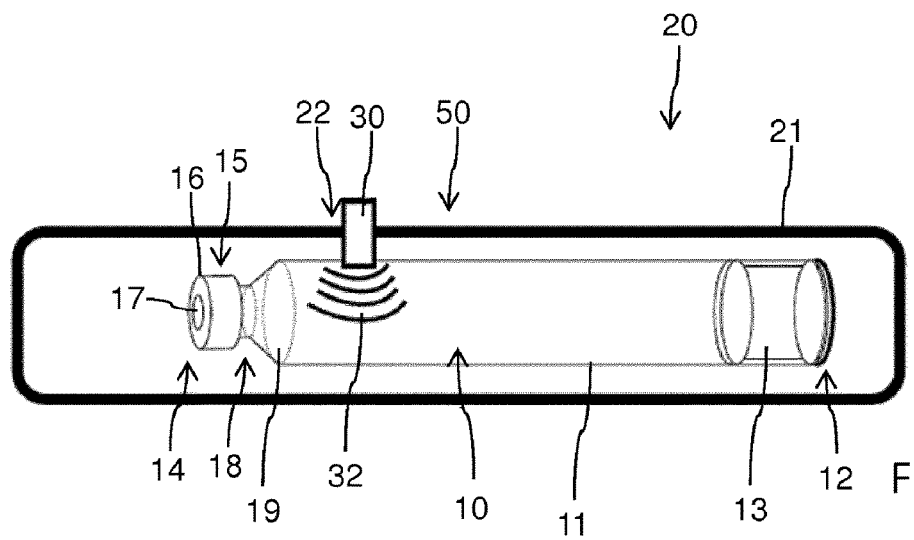
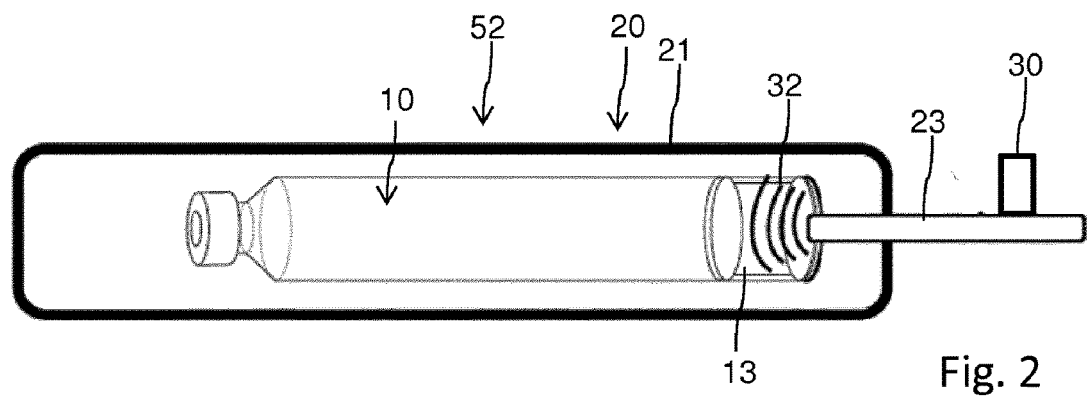
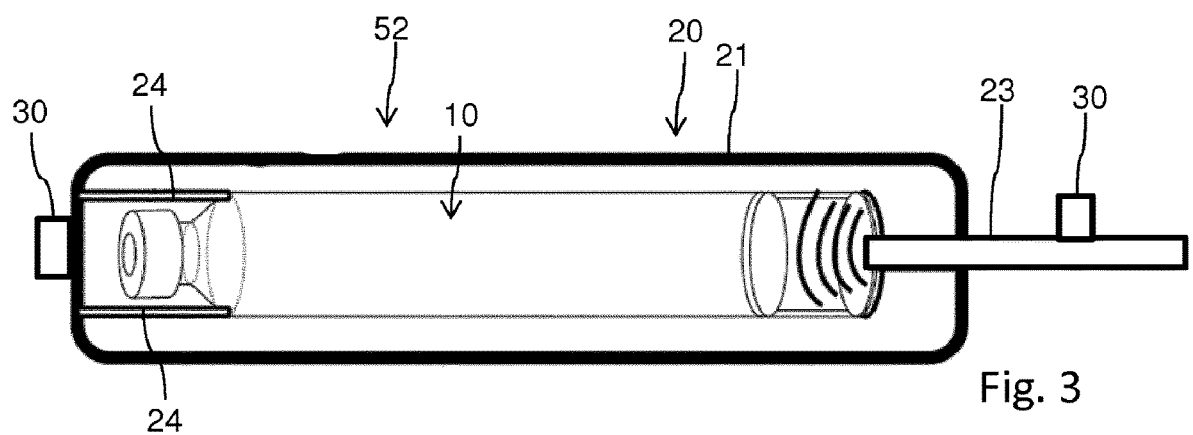

METHOD AND ARRANGEMENT FOR ACOUSTICALLY TESTING THE MECHANICAL INTEGRITY OF A CARTRIDGE

CROSS-REFERENCE TO RELATED APPLICATIONS

This application is a U.S. national stage application under 35 USC § 371 of International Application No. PCT/EP2015/067903, filed on Aug. 4, 2015, which claims priority to European Patent Application No. 14180349.4 filed on Aug. 8, 2014, the entire contents of which are incorporated herein by reference.

FIELD OF THE INVENTION

The present invention relates to the field of testing cartridges, such like carpules, vials or ampoules that are to be filled with a liquid medicament or that are actually filled with a medicament. In particular, the invention relates to the detection or determination of the structural integrity of cartridges filled with a liquid medicament in a non-destructive and minimally invasive way.

BACKGROUND AND PRIOR ART

Liquid medicaments, such like insulin or heparin or other liquid medicaments such like vaccines that for instance require administering by way of injection, are typically provided and stored in vitreous cartridges, such like carpules, vials or ampoules. With regard to the type of medicament, the material of the cartridge or container has to be inert. Therefore, cartridges made of glass are nowadays typically used for storing and distributing such medicaments.

Glass cartridges comprising a vitreous body of e.g. cylindrical geometry may become subject to fracture if not handled appropriately. In the event of undue care, glass cartridges may break. Even though in industrial filling and packaging processes, glass cartridges or vitreous bodies are generally handled with due care, occasional breakage of particular cartridges may not be entirely prevented. In case a glass cartridge is damaged, respective glass splinters may distribute and the medicament contained in the cartridge may contaminate the environment, in particular neighboring cartridges. In the event, a single glass cartridge is damaged in an industrial manufacturing line, it may become necessary that an entire charge of cartridges has to be visually inspected or discarded at high cost.

In addition, the quality of vitreous barrels or glass cartridges provided form a supplier may be subject to inevitable variations that arise from the glass production or manufacturing process of the respective cartridges.

Macroscopic glass breakage may occur due to a singular or due to repeated impact with a particular force or due to repeated and accumulated enlargement of macroscopic defects, the latter of which are not easily detectable. In typical production or assembly processes, a particular glass cartridge may be exposed to a series of low sized mechanical impacts. Any of these impacts alone does not yet lead to a macroscopic glass breakage. But accumulation of successive impact events may constantly lower the cartridge's integrity. This accumulation of mechanical microcracks or mechanical impact can be denoted as glass memory effect.

Especially with drug delivery devices that are initially equipped with a vitreous cartridge the cartridge has to be assembled in the delivery device during assembly thereof. There, the filled cartridge is inevitably subject to further handling. In a final step of device assembly or during packaging of the device the cartridge may be subject to further mechanical impact which may not damage the cartridge right away but which may harm its integrity on a long term scale. Typically, vitreous cartridges to accommodate a liquid medicament are sealed by e.g. a pierceable septum. In the production and assembly environment not only the vitreous body of the cartridge but also the seal may be subject to almost non-detectable defects that might be uncritical initially. However, such minor damages to the vitreous body, to the seal or to the connection of seal and body may harm the closure integrity of such cartridges on a long term scale.

There exist various methods of testing or determining the glass integrity during or prior to a mass-production, mass-assembly or filling process. Typically, the integrity of a vitreous body can be measured with a selection of tools by applying mechanical stress to the glass body from outside with a well-defined force until the glass body breaks or bursts.

With known non-destructive and non-invasive testing methods, such like optical inspection methods, minor damages, such like micro cracks or similar defects are hardly visible or detectable, e.g. due to low contrast or unfavorable optical inspection conditions. Furthermore, with optical inspection methods the medicament contained in the cartridge is subject to irradiation, which either may harm the medicament or which limits the spectral range of applicable electromagnetic waves. Moreover, some medicaments are light sensitive and have to be stored in colored or dyed cartridges that are generally rather unfavorable and disadvantageous to apply an optical inspection procedure.

OBJECTS OF THE INVENTION

Certain aspects of the present disclosure relate to an improved method of testing the mechanical integrity of a cartridge containing a medicament, to provide a respective testing arrangement and to provide a drug delivery device equipped with such a cartridge and being particularly designed and configured for application of the testing method.

The method of testing and the testing arrangement as well as the modified drug delivery device should be non-invasive and should be substantially inert to the medicament contained inside the cartridge. Moreover, the method of testing, the testing arrangement as well as the drug delivery device should support a precise detection of minor damages and defects not only of the vitreous barrel of the cartridge but also of further cartridge components, such like a proximal or distal seal thereof. In addition, the invention aims to provide a method of testing and a testing arrangement that allows for minimally or non-invasive inspection of cartridges filled with a medicament with a high degree of reproducibility.

SUMMARY OF THE INVENTION

In a first aspect the invention relates to a method of testing the mechanical integrity of a cartridge, wherein the cartridge contains a medicament, typically a liquid medicament or at least a component of a liquid medicament. The cartridge containing the medicament is arranged inside a drug delivery device, such like an injection device, in particular inside a pen-injector. The method comprises the steps of acoustically stimulating the cartridge, measuring of the cartridge's acoustic response to the acoustic stimulation and comparing the acoustic response with a standard response or reference response of an intact cartridge.

Based on the comparison of the acoustic response with a standard response, the mechanical integrity of the cartridge is determined. Acoustically stimulating the cartridge comes along with acoustically exciting the cartridge, typically, by applying sound or sound waves to the cartridge. By exposing the cartridge with acoustic signals the cartridge is stimulated to vibrate and to acoustically respond to the acoustic stimulation. Cartridges of equal and standardized geometry as they are typically used in a mass manufacturing and mass assembly process of drug delivery devices exhibit a characteristic acoustic response. By measuring the acoustic response and by comparing the measured acoustic response with a standard or reference response even cartridges only exhibiting minor defects or damages can be precisely detected and identified in a very precise and reliable way.

Applying acoustic waves or sound waves to the cartridge, i.e. exposing the cartridge to a particular and predefined acoustic signal, leads to an acoustic stimulation of the cartridge and hence to a particular resonance of the cartridge. Measuring of the cartridge's acoustic response therefore corresponds to measuring of the cartridge's acoustic resonance to a particular acoustic stimulation. Comparing a measured resonance or resonance spectrum with a standard resonance or resonance spectrum allows to distinguish damaged cartridges from undamaged and intact cartridges. Sound propagation inside a vitreous barrel of a cartridge, through a distal or proximal seal of the cartridge as well as sound propagation through an interface of vitreous cartridge and distal or proximal seal strongly depends on the integrity of the vitreous barrel itself, the integrity of the proximal and/or distal seal as well as on the integrity of a connection of respective seals with the vitreous body. Assuming that either one of cartridge, seal or connection of cartridge and seal is subject to a defect or malfunction, this will have a measurable and detectable influence on the acoustic response of the cartridge in general.

By measuring and comparing of the cartridge's acoustic response not only damaged cartridges may be distinguished from intact cartridges but also a particular type of damage, e.g. a crack or a microcrack of the vitreous body of the cartridge, of the seal or of the connection of seal and body may each lead to different and distinguishable acoustic responses so that by measuring and analyzing the acoustic response of the cartridge it may already be determined and distinguished whether it is the vitreous body, the seal or the connection of vitreous body and seal which is subject to a damage or malfunction. In this way, the method of acoustically stimulating the cartridge and measuring of its acoustic response to the stimulation not only allows to qualitatively distinguish damaged and intact cartridges but also provides a quantitative approach, what kind of damage is actually present.

The method of testing the mechanical integrity is easily applicable in a mass manufacturing and mass assembly process, so that every drug delivery device is easily inspectable after termination of the assembly process. The acoustic stimulation and acoustic response analysis can be easily conducted at the end of an assembly and packaging process. In this way, even damages that may occur during assembly of the cartridge inside the drug delivery device and/or during packaging of the cartridge in a secondary packaging, such like a card box or other secondary containers can be precisely detected.

In this way, a risk of delivery of damaged cartridges to the market can be further reduced. In effect, patient safety can be further enhanced. The method of acoustic stimulation and acoustic response analysis is also beneficial in that the cartridges and/or the drug delivery devices assembled with respective cartridges do not necessarily have to be arranged in a particular orientation compared to the source of the acoustic stimulation and/or with regard to a detector for measuring the cartridge's acoustic response. Since sound propagation is rather undirected and since the acoustic stimulation as well as the acoustic response are rather omnipresent a relative positioning of an acoustic source, of an acoustic detector and of the drug delivery device with its cartridge is rather uncritical. The method of acoustic stimulation and acoustic response analysis is therefore easily implementable in a mass manufacturing and mass assembly process for drug delivery devices.

According to another embodiment a probe, typically an acoustic probe, which is at least operable to emit acoustic signals is brought in direct contact with the cartridge for directly acoustically simulating the cartridge. In order to bring a probe or a probe head in direct contact with the cartridge the drug delivery device typically comprises a housing featuring a through opening through which the probe may directly access the cartridge. For instance, the housing of the drug delivery device may comprise a cartridge holder or a cartridge holder section having an inspection window through which not only the content and filling level of the cartridge disposed therein is visually inspectable. Moreover, the inspection window of the cartridge holder may be simply designed as a through opening, so that the probe may easily access the cartridge located inside the cartridge holder for acoustically stimulating the same.

The probe is at least configured as a transmitter to apply acoustic signals and acoustic waves to the cartridge. The probe may also be implemented as a transducer, which is operable to transmit and to emit acoustic waves and which is also operable to receive and to detect acoustic waves emanating from the cartridge being in direct contact with the probe. In embodiments, wherein the method of testing should be applied to drug delivery devices packed inside a secondary packaging, i.e., wherein the drug delivery device is located inside a box, the box or the packaging in general may comprise a further through opening through which the probe of a testing arrangement is insertable in order to gain direct access at least to the housing of the drug delivery device and/or to the cartridge located therein.

By bringing the probe in direct contact with the cartridge, a very precise and reliable as well as reproducible acoustic stimulation of the cartridge can be obtained. In this way, acoustic response or acoustic resonances from further components of the drug delivery device can be depleted or reduced, so that the measurable acoustic response is based on the acoustic response of the cartridge to a large or major degree.

According to another embodiment a device component of the drug delivery device is in direct mechanical contact with the cartridge. Here, the probe of a testing arrangement is coupled with the device component for indirectly acoustically stimulating the cartridge. There are at least some device components, which upon a final assembly of the drug delivery device are in direct mechanical contact with the cartridge. It is conceivable, that a housing component, such like a cartridge holder, is in direct mechanical contact with the cartridge assembled therein. The cartridge holder may comprise a particular support structure at an inside-facing sidewall portion or at a distal housing portion to directly engage with the cartridge.

It is conceivable, that the cartridge is clamped or positively locked inside the cartridge holder, so that a tight fitting of cartridge and cartridge holder of the drug delivery device is attained. The cartridge holder then acts as an acoustic conductor or wave guide to transfer at least an acoustic stimulation from the probe to the cartridge. It is further conceivable, that the cartridge holder not only transfers acoustic waves towards the cartridge but that the cartridge holder also transfers and guides the cartridge's acoustic response back to the probe or to some other acoustic detector which is either in direct contact with the cartridge holder or which is arranged in a contactless configuration in regard to the cartridge holder.

There are some further device components, such like a piston rod, which may be in direct axial abutment with a piston, hence with a proximal seal of the cartridge in a state of final assembly of the drug delivery device. It is then conceivable, that an acoustic stimulation or excitation is transferred to the cartridge via the piston rod. In general, there are many different ways in order to establish a mechanical contact between the cartridge and at least one further device component. Depending on the particular arrangement of the cartridge inside the drug delivery device, a particular reference response of an intact cartridge may be previously recorded and stored and may serve as a kind of a fingerprint that is to be compared with acoustic responses of a series of cartridges to be inspected with the present method.

According to another embodiment the probe of the testing arrangement is coupled with a drug delivery device's housing. Here, the housing of the drug delivery device is acoustically coupled to the device component that is in direct mechanical contact with the cartridge. In this embodiment, a further indirect acoustic stimulation of the cartridge is attained. First, the probe acoustically stimulates the housing of the drug delivery device, which through its mechanical coupling with a device component acoustically stimulates the respective device component, which in turn, through its direct mechanical contact with the cartridge, acoustically stimulates the cartridge.

In the same or in a similar way, the acoustic response of the cartridge may be transferred to the housing, such that the acoustic response is detectable either directly with the probe or with a further detector being either in direct mechanical contact with the housing or being located outside the drug delivery device.

Acoustic stimulation and measuring or recording of the cartridge's acoustic response may take place at the same time or within overlapping time intervals. However, it is also conceivable, that the acoustic response is detected and analyzed with a certain time delay compared to the acoustic stimulation. In this way, not only the direct and instant response of the cartridge but also its resonating and acoustic damping as well as an after response can be detected and analyzed, which may be equally or additionally used to detect and to determine the integrity of a particular cartridge.

According to another embodiment, the acoustic stimulation comprises emitting of a series of acoustic signals of different frequency. Typically, a whole spectrum of stimulating frequencies is to be applied to the cartridge. Typically, the acoustic stimulation includes or comprises a whole spectrum of acoustic excitation frequencies. The acoustic stimulation may comprise a frequency sweep, wherein the frequency of an acoustic stimulation signal is either continuously modified or wherein the frequency is modified stepwise. The frequency range may include audible frequencies, such like a frequency spectrum ranging from 2 Hz to 20 kHz. Alternatively or additionally a series of different frequency spectra is applicable to acoustically stimulate the cartridge. Depending on the resonance behavior and the eigenfrequency of the cartridge and its cartridge components, such like barrel, distal and proximal seal, the stimulation frequencies may also include an ultrasound spectrum. Hence, frequencies of a frequency range larger than 16 kHz and up to 100 kHz or hundreds of kHz are equally applicable to acoustically stimulate the cartridge.

Making use of a whole spectrum of acoustic stimulating waves allows to acoustically inspect the cartridge not only in regard to a single and a particular acoustic wavelength but to a whole series of different wavelengths. Accordingly, the whole spectrum of the acoustic response can be inspected and exploited in order to compare the measured acoustic response with a standard or reference response of an intact cartridge. Analysis of a whole spectrum of the cartridge's acoustic response increases reliability and precision of the testing method in general.

According to a further embodiment, comparing of the acoustic response is conducted on the basis of a power spectrum of the measured acoustic response and on the basis of a power spectrum of a standard response or reference response of an intact cartridge. The power spectrum generally describes, how the variance of the response of the cartridge, in particular of an oscillation or resonance as a function of time is distributed over frequency components. Especially the analysis of the power spectrum of recorded or measured acoustic response of the cartridge is indicative of eventual damages or defects thereof.

The power spectrum is obtainable from the measured acoustic response, e.g. through recording the acoustic response by a microphone or some other sound transducer and by way of transferring the recorded acoustic response into respective electrical signals. These electrical signals may be sub-converted into digital signals. Moreover, the electrical signals representing the acoustic response of the cartridge may be subject to at least one or several filter functions. For providing and generating a power spectrum the electrical signals representing the acoustic response of the cartridge may be subject to a Fourier transformation, typically they may be subject to a fast Fourier transform (FFT) to be conducted by electronic components of a testing arrangement.

Based on the power spectrum further testing and comparing algorithms may be applied in order to compare the measured power spectrum with a reference power spectrum representing an intact cartridge. Here it is even conceivable, that a large series of standard responses are stored in a memory of the testing arrangement, wherein the standard responses may not only represent intact cartridges but also cartridges exhibiting a particular damage.

By comparing measured acoustic responses with recorded and stored reference responses representing intact or damaged cartridges, a respective decision can be made, whether the measured acoustic response matches with the response of an intact cartridge or with a response of a damaged cartridge. It is even conceivable, that the comparison provides only a certain likelihood of a damage and hence generates a probability whether or not the measured or recorded acoustic response represents a damaged or an intact cartridge. Based on a likelihood it is conceivable, that the method conducts further analysis of the measured acoustic response in order to determine and to distinguish whether the investigated cartridge comprises a damage or not.

It is even conceivable, that particular peaks in the power spectrum are representative for particular damages or defects of the cartridge. Hence, for detecting of a particular type of defect it may be already sufficient to record the power spectrum and to further analyze only a single or a few characteristic frequencies thereof in order to detect a damaged or defect cartridge.

According to another aspect the invention also relates to a drug delivery device for administering a liquid medicament. The drug delivery device may be implemented as an injection device, such like an injection pen. The drug delivery device comprises a housing and a cartridge filled with the medicament, wherein the cartridge is arranged inside the housing. In addition, the drug delivery device comprises at least one of a direct coupling and an indirect coupling to acoustically stimulate the cartridge from outside the device by means of a probe of a testing arrangement, wherein the probe is at least operable to emit acoustic signals. The drug delivery device may comprise only one of a direct or an indirect coupling or may comprise both, a direct coupling as well as an indirect coupling to acoustically couple cartridge and probe.

The direct and indirect coupling are particularly designed and configured for sound guiding and sound propagation between a probe of the testing arrangement and the cartridge located inside the housing of the drug delivery device. Direct and indirect coupling are particularly configured to provide optimized sound propagation and an acoustic coupling between the cartridge located inside the drug delivery device and the probe of the testing arrangement, which may be located outside the drug delivery device or which may only partially reach or extend into the drug delivery device.

The drug delivery device therefore distinguishes from known and conventional drug delivery devices by its direct or indirect acoustic coupling, which is particularly configured and designed to provide an acoustic bridge between the cartridge and the probe of the testing arrangement. Hence, the drug delivery device, its housing or particular device components thereof require a geometric or functional modification in order to act or to support the direct or indirect coupling of the drug delivery device.

According to a further embodiment the direct coupling comprises a through opening in the housing of the drug delivery device to receive the probe and to bring the probe in direct contact with the cartridge located inside the housing. The through opening in the housing may be provided by an inspection window of a cartridge holder or by a cartridge holder portion of the drug delivery device's housing. Moreover, the housing of the drug delivery device may comprise a separate through opening, particularly adapted and configured to receive the probe and to bring the probe in direct contact with the cartridge located inside the housing.

By inserting the probe through the housing's through opening, a direct mechanical contact between the probe and the cartridge can be established in order to acoustically stimulate the cartridge by means of the probe. In this way, acoustic stimulation and acoustic excitation of the drug delivery device or components thereof can be substantially reduced, thereby improving a contrast and/or a signal quality of the measurable acoustic response detectable by an acoustic sensor.

In another embodiment the indirect coupling comprises at least one device component that is in direct contact with the cartridge. Here, the device component is further acoustically coupled to the housing. The device component is particularly mechanically or rigidly connected to the housing. It is even conceivable, that the device component is configured and designed as an integral component of the housing. For instance, the device component may comprise a piston rod in axial abutment with the cartridge. In other embodiments the device component may comprise a distal support to directly engage with the vitreous barrel of the cartridge.

Further embodiments of the indirect coupling include fasteners by way of which the cartridge is rigidly attached to the housing of the drug delivery device. The device component may particularly serve to provide a well-defined fixing of cartridge and housing of the drug delivery device. The at least one device component may be configured to clamp the cartridge inside the housing or to press-fit the cartridge inside the housing. By means of the acoustic stimulation and acoustic response analysis it could be even determined, whether the cartridge is subject to inadmissible tension or mechanical load in its assembly configuration inside the housing of the drug delivery device.

Applying a mechanical load, e.g. for clamping the cartridge may alter the acoustic response of the cartridge. This could result in a frequency shift in the power spectrum derived from the measured acoustic response of the cartridge. If a respective frequency shift should be above a predefined level or threshold, this could be a clear indication for that an intact cartridge is assembled in an inappropriate way inside the drug delivery device, in which the cartridge might be subject to inadmissible mechanical load.

Furthermore and according to another embodiment it is conceivable, that the cartridge is mechanically engaged or connected with a sound absorbing or sound transferring medium. In particular, the cartridge may be assembled inside a mount equipped or provided with a particular sound absorbing or sound sensitive material. For instance, the cartridge may be mechanically coupled to a pouch or to a bag filled with a gel exhibiting a particular acoustic response or particular acoustic properties. For instance, the cartridge could be at least in sections coupled with or wrapped inside a gel coating or a gel cushion. In this way, even a mechanically contactless acoustic coupling of a probe located outside the drug delivery device and the cartridge in acoustic or mechanical contact with the gel material could be established. In particular, such a gel-containing mount of the cartridge can be easily acoustically stimulated by the probe thereby transferring respective acoustic signals to the cartridge in well-defined and reproducible way.

In this way a mount for the cartridge may form an indirect mechanical coupling to the probe even without establishing a specific mechanical contact between the probe and the housing of the drug delivery device.

According to a further embodiment the indirect coupling comprises at least one device component that is in direct contact with the cartridge and which is directly or indirectly coupled with the housing or with a further device component extending through or outside the housing. Here, it is particularly conceivable, that e.g. a piston rod is in direct contact with the cartridge. The piston rod may be further in direct or indirect but permanent mechanical contact with at least one further device component, such like a dose button. The dose button may be located at a proximal end of the housing of the drug delivery device. It may even protrude proximally from the proximal end of the housing. It is particularly conceivable, that the device component in direct contact with the cartridge does not itself protrude from the housing but that the particular device component in direct contact with the cartridge is mechanically connected with at least one or several further device component, wherein the further device component extends through and/or outside the housing of the drug delivery device. It would then be possible to mechanically connect the probe of the testing arrangement with this further device component in order to indirectly transfer an acoustic stimulation to the cartridge.

It is generally to be mentioned, that the drug delivery device is particularly configured and adapted to cooperate and to mate with a probe of the testing arrangement as described below in order to conduct the method of testing the mechanical integrity of the cartridge as further described above. Hence, any features, benefits and effects described in conjunction with the method of testing and/or with the testing arrangement equally apply to the drug delivery device and vice versa.

According another aspect the invention also relates to a testing arrangement for testing of the integrity of a cartridge containing a medicament. The cartridge is arranged inside a drug delivery device, such like an injection pen or other delivery devices, such like an infusion device, an infusion pump or an inhaler. Typically, the testing arrangement is configured for testing of a cartridge arranged inside a drug delivery device as described above.

The testing arrangement comprises a probe for acoustically stimulating the cartridge. The testing arrangement further comprises a sensor for measuring the cartridge's acoustic response to the acoustic stimulation induced by the probe. The testing arrangement further comprises at least a processor to compare the acoustic response with a standard response, hence with a reference response of an intact cartridge. The processor is further operable to determine the mechanical integrity of the cartridge on the basis of the comparison.

Generally, the testing arrangement is implementable in a mass manufacturing or mass assembly process, wherein the drug delivery device during its assembly is equipped with at least one cartridge. The testing arrangement is particularly operable to conduct the above described method of testing the mechanical integrity of a cartridge. The probe is particularly configured to get in direct contact with the cartridge or to get in direct mechanical contact with a device component, which itself is in direct contact with the cartridge. The geometry of the probe is particularly adapted to the geometry and shape of the drug delivery device and/or of the cartridge in order to directly or to indirectly stimulate the cartridge with acoustic waves.

In general, acoustic stimulation of the cartridge may also occur via sound propagation through air. Hence, the acoustic stimulation of the cartridge does not necessarily require to establish mechanical contact between the probe and the cartridge in a direct or indirect way. However, a direct contact of probe and cartridge or a sound-transferring contact between probe and cartridge via at least one device component seems to be beneficial for an effective stimulation and acoustic excitation of the cartridge. Damping losses as well as sound reflections on surfaces of the drug delivery device and its components can be reduced in this way.

According to another embodiment the probe is operable to stimulate the cartridge with a series of acoustic signals of different frequency. In particular, the probe is operable to apply a whole spectrum of acoustic signals to the cartridge. Typically, the probe is operable to emit a continuous or a discrete acoustic spectrum and to apply respective acoustic waves to the cartridge. In this way, the acoustic response of the cartridge can be inspected and detected over a comparatively large range of frequencies.

According to another embodiment the processor of the testing arrangement is operable to generate a power spectrum of the cartridge's acoustic response. By means of a power spectrum generation, a precise and reliable analysis of the cartridge's acoustic response to a series of acoustic signals of different frequency can be conducted, which generally increases the precision and reliability of the testing results achievable with the testing arrangement. In addition, the processor is generally applicable not only to generate a power spectrum but also to conduct analogue digital conversion of recorded and measured acoustic signals as well as to apply at least one or a series of filter functions that may help to improve to identify the acoustic contribution of the cartridge in the acoustic response, recorded and measured by an acoustic detector, which inevitably also records and measures an acoustic response of the drug delivery device.

Since the drug delivery device may be composed to a large extent of plastic components, the acoustic response of the drug delivery device and/or of its components may drastically differ from the acoustic response of the cartridge, which typically comprises a vitreous cartridge sealed with elastomeric sealing members and which may be fastened to the cartridge by means of a metal cap or the like fasteners.

According to a further embodiment the probe is operable to emit acoustic signals and the probe is further operable to detect and to capture the cartridge's acoustic response. In this embodiment the probe is implemented as an acoustic transducer being operable to generate and to broadcast or to transmit acoustic signals as well as to measure and to capture acoustic signals, which typically emanate from the cartridge in response to the acoustic stimulation. The frequency range and the amplitude or power of the acoustic signals emitted and detected or captured by the probe strongly depend on the acoustic response characteristics, hence on the acoustic fingerprint of the cartridge.

It might be of particular benefit to make use of acoustic frequencies that are located outside the audible spectrum. In this way, persons located in direct vicinity to the testing arrangement may not be harmed or influenced by the operation of the testing arrangement. Moreover, operating the testing arrangement in a non-audible frequency range may be also beneficial for the detection and measuring of the cartridge's response. In this way, other audible noise, which is inevitably present in a production and assembly environment would then be outside the detection range or outside a spectral range of interest of the testing arrangement.

In this context it is to be mentioned, that the testing arrangement is closely correlated to the above described testing method and to the drug delivery device. Hence, any features, benefits and effects described in conjunction with the method of testing and/or with the testing arrangement equally apply to the drug delivery device and vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(0)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, an exemplary embodiment of the present invention is described in detail by making reference to the drawings, in which:

FIG. 1 schematically shows an embodiment of a drug delivery device apt and configured to be subject to acoustic stimulation and acoustic response analysis of a cartridge assembled therein, FIG. 2 schematically shows another embodiment of a drug delivery device, wherein a piston rod actually serves as an indirect acoustic coupling between a probe and the cartridge, FIG. 3 schematically shows a further embodiment, wherein the cartridge is rigidly attached and hence acoustically coupled with the housing of the drug delivery device.

DETAILED DESCRIPTION

Figure 11:
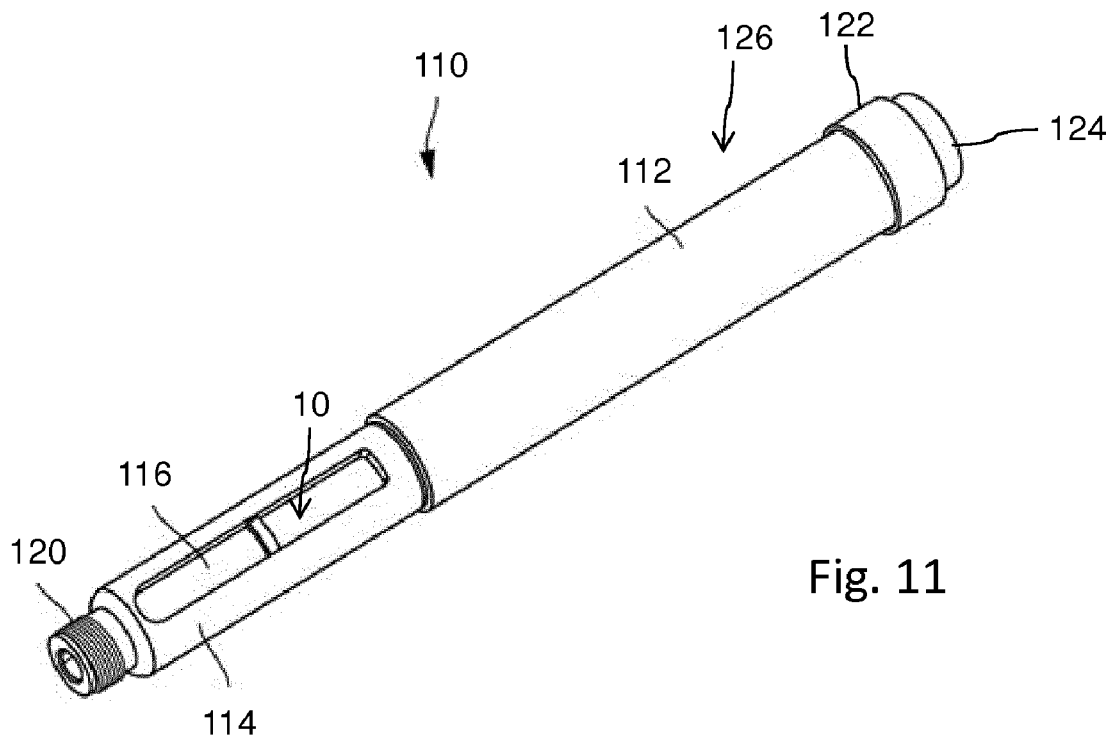

In FIG. 11 a schematic perspective view of a drug delivery device 110 is provided. The drug delivery device 110 is configured as an injection device, in particular as a pen-type injector. The drug delivery device 110 comprises a body 112 acting or serving as a proximal housing component. Here, the body 112 of the drug delivery device 110 is of sleeve-like or tubular shape. At its distal and hence at its dispensing end, the drug delivery device 110 comprises a cartridge holder 114 having an inspection window 116 through which the content of a cartridge 10 located inside the cartridge holder 114 is visually inspectable. At its distal end the cartridge holder 114 comprises a threaded socket 120 configured to releasably engage with a correspondingly threaded needle assembly.

Mounting of a needle assembly, which is not illustrated, to the distal end of the cartridge holder 114 provides access to the interior of the cartridge 10 located and fixed inside the cartridge holder 114. In this specific embodiment cartridge holder 114 and proximal body 112 might be non-detachably interconnected. In particular, the drug delivery device 110 may be configured as a disposable drug delivery device. After consumption of the content of a cartridge 10 the entire drug delivery device 110 is to be discarded. The disposable type of the drug delivery device 110 requires that the cartridge 10 filled with the medicament assembled inside the device 110 as it enters the market and as it is delivered to customers or patients.

The cartridge 10 is shown in more detail in FIG. 1. For reasons of simplicity, the arrangement of housing 112 and cartridge holder 114 of the drug delivery device 110 is illustrated and represented by a rather generic housing 21 as it is shown in FIGS. 1-6. In this context it has to be further noted, that the illustration of a drug delivery device 110 according to FIG. 11 is only exemplary and that the present invention is universally applicable to a large variety of drug delivery devices of different type as well as to different shapes and geometries of housings 21 thereof. The representation of the drug delivery device 20 with a housing 21 as shown in FIGS. 1-6 may include a single and unitary housing as well as a two-component housing as shown in FIG. 11 consisting of cartridge holder 114 and proximal housing component or body 112.

As shown in more detail in FIG. 1, the cartridge 10 located inside the housing 21 of the drug delivery device 20 comprises a barrel 11 of tubular shape. The barrel 11 is typically made of a vitreous material that is substantially inert in regard to the medicament contained inside the cartridge 10. Typically, the barrel 11 is made of glass. The proximal end 12 of the barrel, i.e. the end that is located on a side opposite to a dispensing end of the cartridge 10 is effectively sealed by means of a piston 13 of elastomeric material. The piston 13 is displaceable in axial direction inside the cartridge 11. The piston 13 is sealingly engaged with the inside-facing sidewall portion of the barrel 11. The distal end 14 of the cartridge 10 comprises a stepped down neck portion 18. The tubular-shaped barrel 11 comprises a distal shoulder part 19 forming the neck portion 18 and which shoulder part 19 may be of a conical or conical-like shape. The diameter-reduced distal end 14 of the cartridge 10 is sealed with a pierceable septum 17 that is mechanically fixed to the cartridge's distal end 14 by means of a cap 16.

For dispensing and for injecting a medicament the needle assembly (not illustrated) is attached to the housing 21 of the drug delivery device thereby piercing the septum 17, hence the distal seal 15 of the cartridge 10 in order to access the interior of the cartridge 10. Applying a distally-directed pressure onto the piston 13, e.g. by means of a piston rod, which may be represented by the device component 23 according to FIGS. 2 and 3 the piston 13 is displaceable in distal direction, thereby increasing a fluid pressure inside the cartridge 10 to expel a predefined amount, hence a dose of the medicament by way of the fluid transferring connection of cartridge 10 and needle assembly.

The drug delivery device 20 may be equipped with a drive mechanism 126 as it is indicated with the drug delivery device 110 according to FIG. 11. The drive mechanism 126 is operable to advance a piston rod in distal direction. The drive mechanism 126 is further operable to set a dose of variable size and to subsequently trigger or to conduct a dispensing action, by urging the piston rod in distal direction. The drive mechanism 126 typically comprises numerous mechanically interacting components. Moreover, the drive mechanism 126 typically comprises a dose dial 122, by way of which a user may individually select and set a dose of variable size. The drive mechanism 126 may further comprise a dose button 124 by way of which the previously set dose of a medicament may be dispensed and injected in a controlled way. Typically, the dose dial 122 is actuated or rotated by a user in order to set a predefined dose of a medicament while the dose button 124 is configured to be depressed in distal direction in order to trigger a dose dispensing action.

Figure 7:
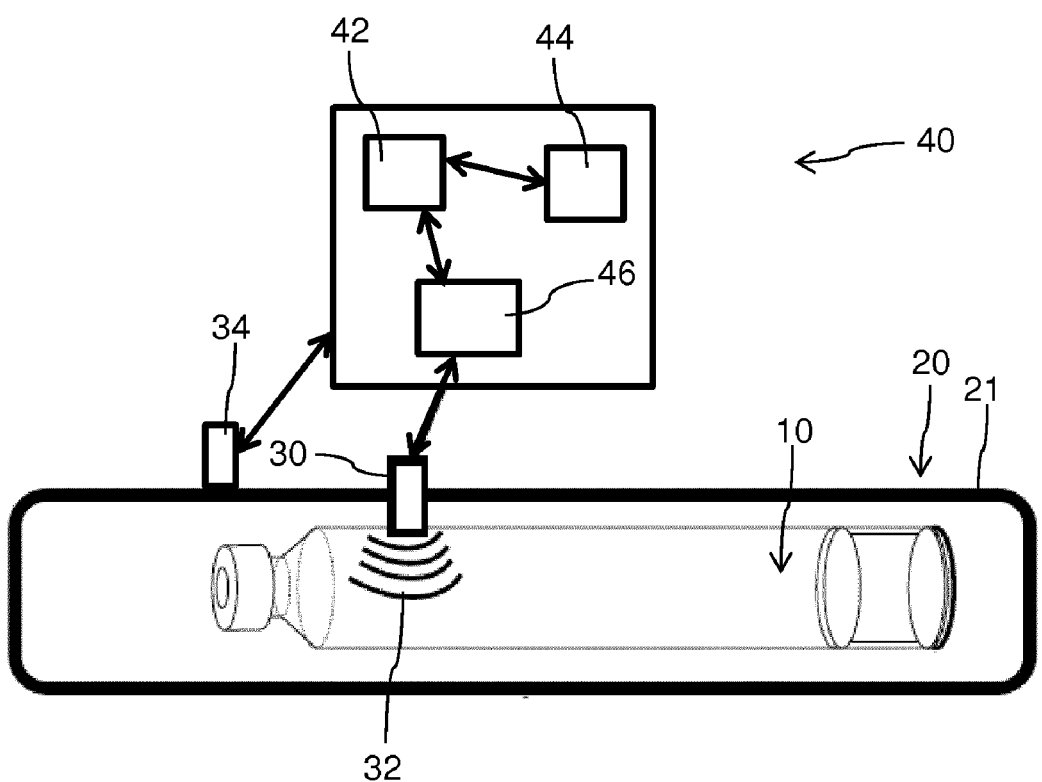
Figure 10:
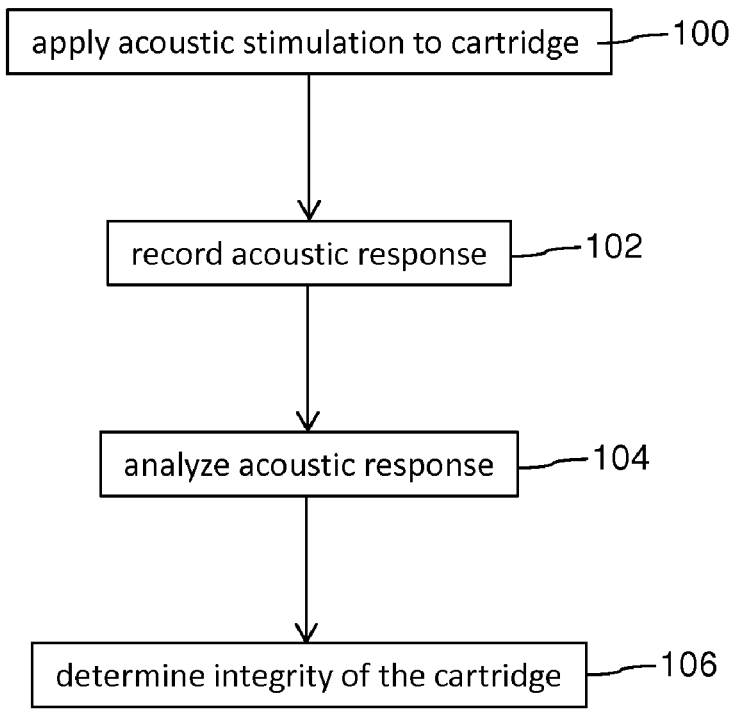
FIG. 10 shows a flowchart of the method of testing the mechanical integrity of the cartridge located inside a drug delivery device and FIG. 11 schematically shows an example of a drug delivery device of pen-injector type.

In the following the method of testing the mechanical integrity of the cartridge 10 is described. The method as indicated by the flowchart according to FIG. 10 comprises a first step 100, wherein an acoustic stimulation is applied to the cartridge 10, typically by making use of a probe 30 of a testing arrangement 40 as shown in FIG. 7. Thereafter, in step 102 the acoustic response of the cartridge 10 is recorded or measured, typically by making use of an acoustic sensor 34 or by the probe 30. Thereafter in step 104, the acoustic response, in particular the signals obtained via the probe 30 and/or via the sensor 34 are analyzed in order to determine in a final step 106 whether the inspected cartridge 10 is intact or exhibits a damage or defect.

Analyzing of the acoustic response includes a comparison of the acoustic response measured by the sensor 34 or probe 30 with a standard acoustic response of an intact cartridge, that serves as a reference response. In order to automatically conduct the method of testing the mechanical integrity of the cartridge 10 the testing arrangement 40 comprises an input/output port 46 that is connected with at least one of the probe 30 and the acoustic sensor 34. The input/output port 46 is further connected with a processor 42 that is operable to conduct the analysis of the measured acoustic response of the cartridge 10. Furthermore, the testing arrangement 40 is equipped with a storage 44, in which at least one standard response or a respective reference response is stored for enabling a comparison of measured acoustic responses with typical responses of intact cartridges 10.

Figure 8:
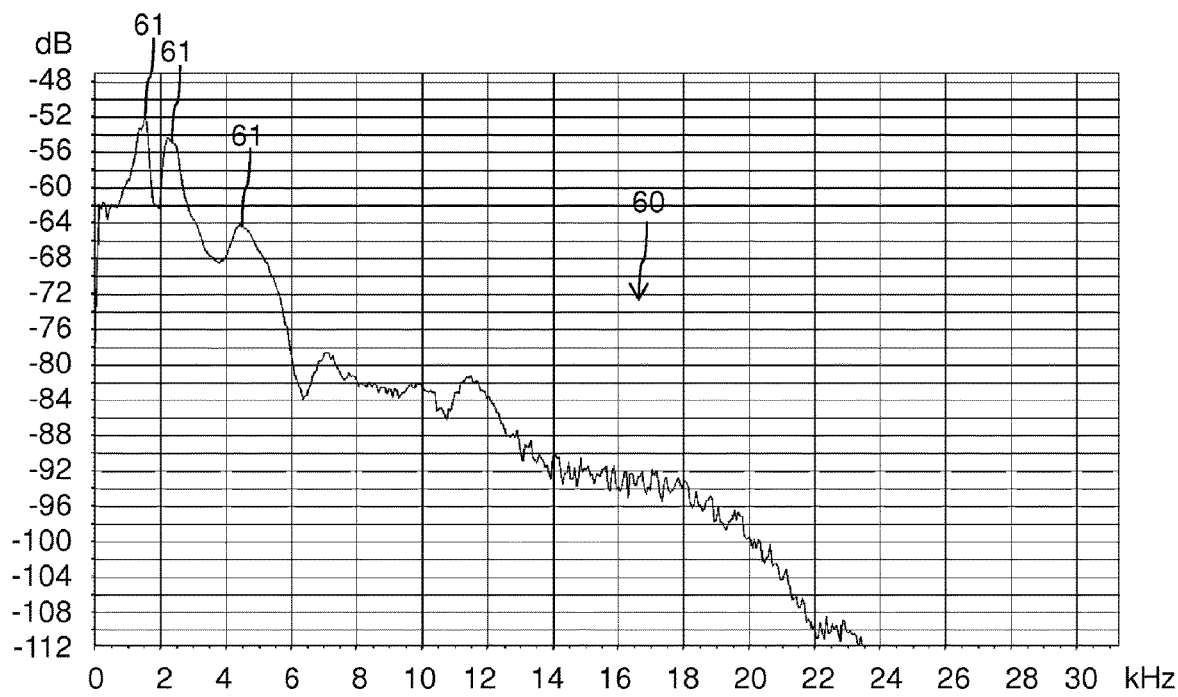
FIG. 8 shows a power spectrum of an acoustic response of a cartridge.

A measured acoustic response 60 of a damaged cartridge 10 is exemplary illustrated in FIG. 8 representing a power spectrum of an acoustic response 60 of a cartridge 10 that has been exposed to an acoustic spectrum ranging from 20 Hz to 20 kHz. In the illustrated experiment the wave form of the acoustic stimulation is of sinusoidal type and the frequency spectrum was swept over a time interval of 0.2 seconds. The acoustic response 60 of the cartridge 10 as illustrated in FIG. 8 exhibits various distinct peaks 61 that are generally usable to characterize the mechanical integrity as well as a closure integrity of the cartridge 10.

Figure 9:
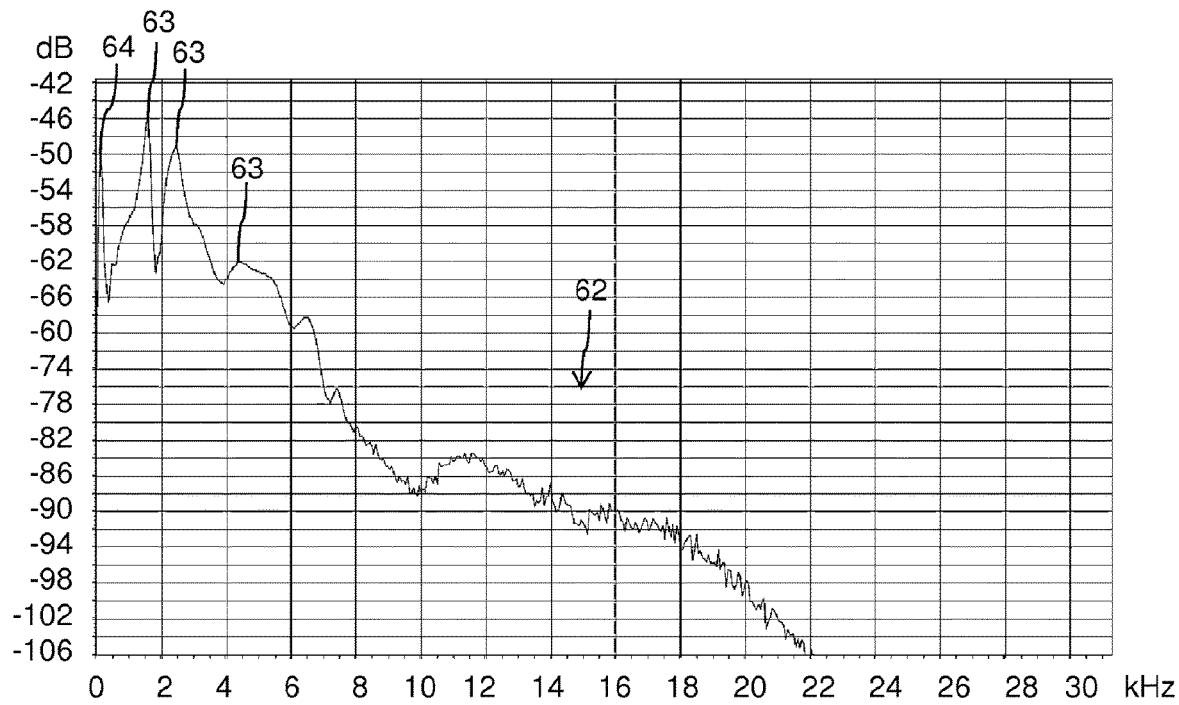
FIG. 9 shows a power spectrum of a standard response of an intact cartridge that represents a reference power spectrum.

In FIG. 9, a reference or standard response 62 is illustrated in a comparable power spectrum. Also the standard response 62 exhibits various distinct peaks 63 that substantially match with the peaks 61 of the acoustic response 60 according to FIG. 8. IN the illustrated exampled the standard response 62 according to FIG. 9 exhibits specific peak 64 at about 120 Hz, which has no corresponding equivalent or counterpart in the measured acoustic response 60 according to FIG. 8. Since the measured acoustic response 60 of the inspected cartridge 10 is void of a distinct peak in the region of 120 Hz this is a clear and unequivocal indication that the acoustic response 60 differs from the standard or reference response 62 thereby indicating, that the inspected cartridge has at least a small damage or defect.

For practical implementations of the method of testing and for deploying and installing the testing arrangement it is of particular benefit that the testing arrangement is sufficiently and precisely acoustically coupled with the drug delivery device 20 and/or with the cartridge 10 located therein. In FIGS. 1-6 various approaches to establish a well-defined and reproducible acoustic coupling between the probe 30 and the cartridge 10 are illustrated. Here, one may distinguish between a direct coupling and an indirect coupling of probe 30 and cartridge 10.

In the embodiment according in FIG. 1, the housing 21 of the drug delivery device 20 comprises a through opening 22 in a sidewall portion through which the cartridge 10, in particular its vitreous barrel 11 is directly accessible for the probe 30. The probe is operable to transmit acoustic signals 32 in order to induce an acoustic response of the cartridge 10 revealing its mechanical integrity. Such a through opening 22 may be directly provided or may coincide with an inspection window 116 of a cartridge holder 114 as exemplary illustrated with the drug delivery device 110 according to FIG. 11. In this embodiment, the geometry, hence the size and outer dimensions of the probe 30 match and correspond to the size of the through opening 22. By means of this type of direct coupling 50 as indicated in FIG. 1, the cartridge 10 can be unalterably and rather directly acoustically stimulated by means of the probe 30 that is typically implemented as an acoustic transducer. In this way probe 30 and cartridge 10 are mutually acoustically coupled via a direct coupling 50.

In the embodiment according to FIG. 2, an indirect coupling 52 between probe 30 and cartridge 10 is implemented. There, a device component 23, e.g. in form of a piston rod is shown, which is in direct mechanical contact with the cartridge 10. In an assembly configuration of the drug delivery device 20, in particular of a disposable drug delivery device the device component 23, e.g. the piston rod, is in direct abutment with at least the piston 13 of the cartridge 10. It is then intended that the device component 23 is subject to acoustic stimulation or acoustic excitation. In this way, the device component 23 acts as an acoustic waveguide to provide an acoustic stimulation or acoustic excitation of the cartridge 10.

As shown in FIG. 3, acoustic stimulation of a piston rod may be conducted via a further device component 28, e.g. configured as a dose button 124 located at a proximal end of the housing 21. Such a device component 28 may be directly or indirectly but permanently engaged with a piston rod 23. An acoustic stimulation of the dose button 124 then leads to a respective acoustic stimulation of the cartridge 10 when assembled inside the device and when in direct abutment with the piston rod 23. The piston rod 23 and the dose button 124 are made of a particular ultrasound transmitting plastic material. Their acoustic impedance, in particular their ultrasonic impedance may mutually match.

In the further embodiment as shown in FIG. 3 the cartridge 10 is rigidly coupled or rigidly engaged with the housing 21, e.g. by means of a device component 24 acting as a bearing to engage with the shoulder portion 19 of the cartridge's 10 distal end 14. By means of the device component 24 or by means of several device components 24 extending inwardly from the housing 21 and directly engaging with the cartridge 10 a well-defined transfer of acoustic excitation of the housing towards and into the cartridge 10 can be provided. Typically, the cartridge 10 is tightly fitted or tightly engaged with the device components 24. In the embodiment according to FIG. 3 it is intended, that the probe 30 is in direct mechanical contact with the housing 21 of the drug delivery device 20.

The bearing and hence the device component 24 may be located inside a cartridge holder or cartridge holder section of the housing 21, which is particularly configured to accommodate the cartridge 10. The bearing 24 and at least a portion of the housing 21 may comprise a particular ultrasound transmitting plastic material. The plastic material may be provided with ultrasound transmitting particles embedded therein. Hence, in the bulk of the housing 21 and/or of the bearing 24 there may be embedded particular ultrasound transmitting particles. Such particles may exhibit a well-defined and pronounced acoustic response or resonance when exposed to ultrasound of a given frequency.

Figure 4:
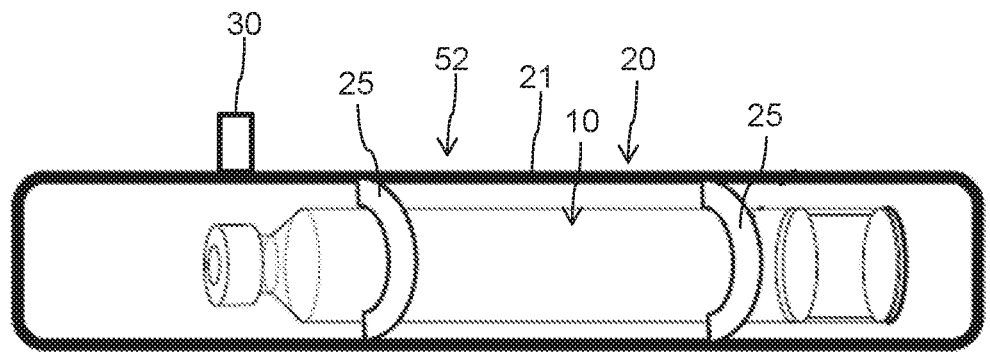
FIG. 4 shows a further embodiment of a mutual mechanic and acoustic coupling of cartridge and housing.

In the embodiment according go FIG. 4, two annular-shaped device components 25 separated in axial direction are configured to serve as a mount for the cartridge 10 inside the housing 21 of the drug delivery device 20. The device components 25 may act as O-rings and may serve to clamp and to rigidly fasten the cartridge 10 to the inside-facing sidewall portions of the housing 21. In this way, another well-defined mechanical engagement and hence as respective acoustic coupling of housing 21 and cartridge 10 can be established.

Figure 6:
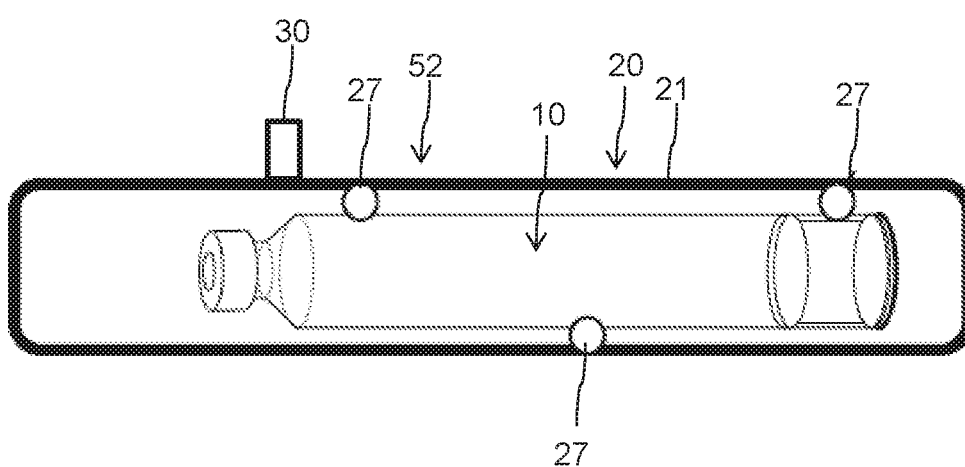
FIG. 6 shows a further embodiment of the drug delivery device, wherein the cartridge is clamped and wherein the cartridge is mechanically as well as acoustically coupled to the housing, FIG. 7 schematically depicts a testing arrangement for testing the integrity of the cartridge located inside the drug delivery device.

In a similar way, FIG. 6 shows three device components 27 of knob-like or nipple-like shape that are arranged at an axial distance at selected portions or sections on the inside-facing portion of the housing's 21 sidewall. There, the device components 27 may serve to axially and radially clamp the cartridge 10 inside the housing 21. Also in this way, a well-defined acoustic coupling between cartridge 10 and housing 21 can be established. Depending on the type of cartridge 10 and housing 21 as well as depending on the acoustic properties, in particular depending on the acoustic resonance of housing 21 and cartridge 10 an appropriate mutual clamping or mechanical coupling of cartridge 10 and housing 21 has to be selected in order to optimize the representation and detectability of defects or damages of the cartridge 10 on the basis of its acoustic response 60.

Figure 5:
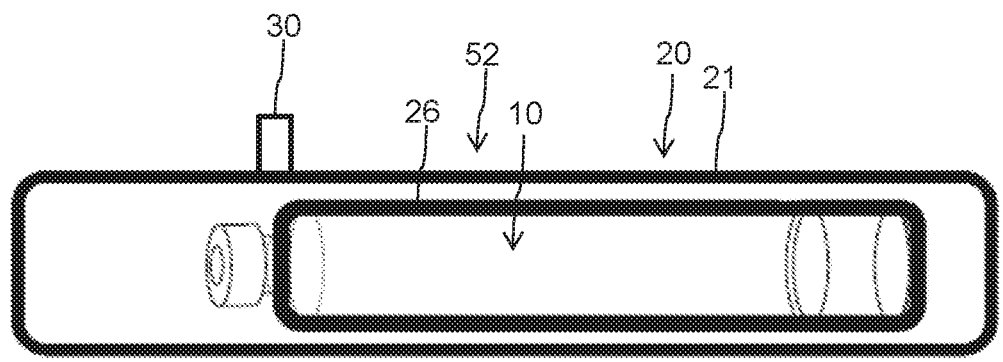
FIG. 5 shows a further embodiment of the drug delivery device having a particular mount for the cartridge that is apt and configured to provide an acoustic coupling between the cartridge and a probe located outside the drug delivery device.

In FIG. 5, another embodiment is shown, wherein a device component 26 serves as a mount or as a receptacle for the cartridge 10. The device component 26 may be provided with a particular sound or acoustically sensitive material, which exhibits a predefined acoustic absorption characteristics or acoustic transfer behavior. For instance, the device component 26 may be equipped with a particular gel or a granular component that is acoustically stimulatable from outside the drug delivery device 20 even without a direct mechanical contact between the probe 30 and the housing 21. The device component 26, in particular its gelly-, granular filling or coating material may provide acoustic amplification or acoustic attenuation of desired or undesired acoustic frequencies, respectively. Moreover, the device component 26 may be also in mechanical contact with the housing 21. It may provide a well-defined and improved acoustic coupling of the cartridge 10 with the housing 21 of the drug delivery device 20.

In further embodiments the device component 26 comprises a hermetic seal, e.g. a liquid-proof and/or gas-proof plastic foil completely surrounding the cartridge 10. The device component may provide an envelope and a closed shell for the cartridge 10 assembled therein. An interspace between the cartridge 10 and the device component, i.e. the plastic foil may be provided or may be completely filled with an ultrasound transmitting gel, thereby forming or constituting a gel pack.

The arrangement of a hermetic seal and an ultrasound transmitting gel for wrapping of the cartridge 10 inside the drug delivery device 20 provides several beneficial effects. By means of the surrounding gel, the cartridge 10 is mechanically suspended inside the drug delivery device 20. In this way the cartridge is mechanically dampened. The gel embedding the cartridge 10 effectively provides mechanical shock absorption. The device and hence the cartridge will become less prone to mechanical shock.

Second, the gel provides thermal insulation for the cartridge. The relatively thick gel layer completely surrounding the cartridge 10 may act like a cool pack. The cartridge 10 assembled inside the device will heat much slower when the device is taken out of a refrigerated area. The device component 26, i.e. the foil and the ultrasound transmitting gel provide a reduced thermal conductivity.

In addition, the cartridge 10 densely packed inside a foil envelope filled with an ultrasound transmitting gel is easily acoustically inspectable by means of a probe extending through or into a through opening 22 of the housing 21 of the drug delivery device 20.

The device component 26 may also comprise a shrinking foil configured to provide a shrinking effect when the cartridge 10 and the gel are arranged inside an envelope formed by the foil. In this way the cartridge 10 can be densely packed inside the foil envelope and the ultrasound transmitting gel.

Instead of a gel pack it is also conceivable that the cartridge is embedded inside a layer or cladding made of or comprising an epoxy resin. Then the resin based cladding provides an acoustic coupling between the cartridge 10 and the housing 21 and/or the probe 30.

Additionally or alternatively it is also conceivable to shrink the cartridge 10 inside a single or multiple layers of sound transmitting or sound-permeable foils. Such foils could be also adhesively attached to the outer circumference of the cartridge's barrel.

The various implementations as shown in FIGS. 2-6 represent an indirect coupling 52 between the cartridge 10 and a probe 30 located outside the drug delivery device 20. The indirect coupling 52 is of particular benefit for a mass manufacturing or mass assembly process since for testing the integrity of the cartridge 10 it is not necessary to establish a well-defined mechanical connection or contact between the probe 30 and the cartridge 10.

This mechanical connection can be enhanced by an ultrasonic tip, e.g. made of metal. Furthermore, it is conceivable to embed at least one or several metal pieces inside the wrapped foil or gel pack. For instance, a metal piece could be arranged or attached to an inside facing portion of a foil envelope or gel pack. When a probe 30 or an ultrasonic tip is then brought in direct contact with an outer surface of the foil in an overlapping configuration with the metal piece an almost direct mechanical or acoustic coupling between the metal piece and the probe 30 can be obtained. Such a metal piece could be embedded in a layer of ultrasound transmitting gel. It is even conceivable that the metal piece is in direct contact with the cartridge 10. Then, an ultrasound transmission from the probe 30 towards the cartridge 10 is even enhanced.

The probe 30 or the ultrasonic tip may also comprise a plastic component. It is conceivable that the through opening 22 is provided with a plastic component or with a particularly small sized gel pack configured for ultrasound transmission. The through opening 22 can be provided in a proximal housing component also accommodating a drive mechanism. Alternatively or additionally, the through opening may be provided in a distally located cartridge holder of the drug delivery device 20 configured and designed for accommodating the cartridge 10.

Moreover, it has to be noted, that the indirect coupling 52 typically provided by any one or several of the device components 23, 24, 25, 26, 27 may act in both opposite directions. The device components 23, 24, 25, 26, 27 may be particularly designed and operable to transfer an acoustic stimulation from the probe 30 to the cartridge 10. In addition, the device components 23, 24, 25, 26, 27 may be also operable and adapted to return the cartridge's acoustic response 60 to the probe 30 and/or to a separate acoustic sensor 34, which sensor 34 may be either in contact with the housing 21 or which sensor 34 may be located remote of the drug delivery device 20.

LIST OF REFERENCE NUMBERS 10 cartridge
11 barrel
12 proximal end
13 piston
14 distal end
15 seal
16 cap
17 septum
18 neck portion
19 shoulder portion
20 drug delivery device
21 housing
22 through opening
23 device component
24 device component
25 device component
26 device component
27 device component
28 device component 30 probe
32 acoustic signal
34 sensor
40 testing arrangement
42 processor
44 storage
46 input/output port
50 direct coupling
52 indirect coupling
60 acoustic response
61 peak
62 standard response
63 peak
64 peak
110 drug delivery device
112 body
114 cartridge holder
116 inspection window
120 socket
122 dose dial
124 dose button
126 drive mechanism

The invention claimed is:

1. A method of testing mechanical integrity of a cartridge containing a medicament and being arranged inside a drug delivery device, the method comprising:
 acoustically stimulating the cartridge,
 measuring an acoustic response of the cartridge to the acoustic stimulation,
 comparing the acoustic response with a standard response of an intact cartridge, and
 determining the mechanical integrity of the cartridge on the basis of the comparison,
 wherein acoustically stimulating the cartridge comprises indirectly acoustically stimulating the cartridge by coupling a probe configured to emit acoustic signals to a device component of the drug delivery device, where the device component is in direct mechanical contact with the cartridge.

2. The method according to claim 1, wherein acoustically stimulating the cartridge comprises emitting a series of acoustic signals of different frequency.

3. The method according to claim 1, wherein the comparing of the acoustic response with the standard response is conducted on the basis of a power spectrum of the measured acoustic response and on the basis of a power spectrum of a standard response of an intact cartridge.

4. A drug delivery device for administering a liquid medicament, the device comprising:
 a housing,
 a cartridge filled with the medicament and arranged inside the housing, and
 an indirect coupling comprising a bearing in direct contact with the cartridge and in direct contact with the housing, wherein the bearing comprises an ultrasound transmitting plastic material, wherein the indirect coupling forms a mount for the cartridge inside the housing and wherein the cartridge is at least one of axially clamped and radially clamped inside the housing by numerous protrusions extending and protruding inwardly from the housing.

5. The drug delivery device according to claim 4, wherein the protrusions extended axially inwardly from a distal end of the housing and engage with a shoulder portion of the cartridge's distal end.

6. The drug delivery device according to claim 4, wherein the protrusions comprise two O-rings separated from each other in axial direction and wherein the two O-rings are configured to clamp and to rigidly fasten the cartridge to an inside-facing sidewall portion of the housing.

7. The drug delivery device according to claim 4, wherein the protrusions comprise numerous knob-shaped or nipple-shaped protrusions separated from each other in axial direction and configured to axially and radially clamp the cartridge inside the housing.

8. A method of testing mechanical integrity of a cartridge containing a medicament and being arranged inside a drug delivery device, the method comprising:
 acoustically stimulating the cartridge,
 measuring an acoustic response of the cartridge to the acoustic stimulation,
 comparing the acoustic response with a standard response of an intact cartridge, and
 determining the mechanical integrity of the cartridge on the basis of the comparison,
 wherein the acoustically stimulating the cartridge comprises indirectly acoustically stimulating the cartridge by coupling a probe configured to emit acoustic signals to a drug delivery device's housing, which is acoustically coupled to a device component of the drug delivery device which is in direct mechanical contact with the cartridge.

9. The method according to claim 8, wherein acoustically stimulating the cartridge comprises emitting a series of acoustic signals of different frequency.

10. The method according to claim 8, wherein the comparing of the acoustic response with the standard response is conducted on the basis of a power spectrum of the measured acoustic response and on the basis of a power spectrum of a standard response of an intact cartridge.

* * * * *